United States Patent [19]

Morita

[11] 4,165,310

[45] Aug. 21, 1979

[54] SCORCH INHIBITED VULCANIZABLE RUBBER COMPOSITIONS CONTAINING CARBAMIC ACID ESTERS

[75] Inventor: Eiichi Morita, Copley, Ohio

[73] Assignee: Monsanto Company, St. Louis, Mo.

[21] Appl. No.: 946,257

[22] Filed: Sep. 27, 1978

Related U.S. Application Data

[63] Continuation-in-part of Ser. No. 929,621, Jul. 31, 1978, abandoned.

[51] Int. Cl.² .............. C08K 5/44; C07C 155/08; C07C 155/09; C07C 155/02
[52] U.S. Cl. .............. 260/45.85 A; 260/45.85 N; 260/45.9 NC; 260/455 A; 260/465 D; 260/780; 560/10; 560/16; 560/17
[58] Field of Search .............. 560/10, 16, 17; 260/45.9 NC, 45.85 A, 45.85 N, 465 D, 455 A, 780

[56] References Cited

U.S. PATENT DOCUMENTS

| 3,344,163 | 9/1967 | Frank et al. .............. 260/455 A |
| 3,562,225 | 2/1971 | Coran et al. .............. 260/780 |
| 3,663,594 | 5/1972 | Brown et al. .............. 560/17 |
| 3,846,466 | 11/1974 | Pallos .............. 260/455 A |
| 3,885,039 | 5/1975 | Pinkowski et al. .............. 260/455 A |
| 3,895,080 | 7/1975 | Son .............. 526/20 |
| 3,950,534 | 4/1976 | Yagihara et al. .............. 260/455 A |
| 3,974,163 | 8/1976 | Coran .............. 260/293.63 |

FOREIGN PATENT DOCUMENTS 49-14533 4/1974 Japan .
396326 8/1923 U.S.S.R. .

Primary Examiner—Veronica P. Hoke
Attorney, Agent, or Firm—Larry R. Swaney

[57] ABSTRACT

A novel class of N-sulfenyl derivatives of di(carbamic acid esters) are described. The new compounds inhibit premature vulcanization of rubber.

46 Claims, No Drawings

SCORCH INHIBITED VULCANIZABLE RUBBER COMPOSITIONS CONTAINING CARBAMIC ACID ESTERS

This application is a continuation-in-part application of patent application Ser. No. 929,621 filed July 31, 1978 now abandoned. This invention relates to improved vulcanizable rubber compositions inhibited from premature vulcanization, to an improved process for inhibiting premature vulcanization of rubber and to polyfunctional carbamic acid esters which are especially potent premature vulcanization inhibitors.

BACKGROUND OF THE INVENTION

Inhibiting prevulcanization of rubber by N-sulfenyl-substituted or N,N-disulfenyl carbamic acid esters is known. Japanese Pat. No. 49-14533. N-Phenyl-N-sulfenyl substituted carbamic acid esters are known pesticides. Russian Pat. No. 396,326. However, heretofore, N-sulfenyl derivatives of di(carbamic acid esters) were unknown.

SUMMARY OF THE INVENTION

According to this invention, a new class of N-sulfenyl derivatives of di(carbamic acid esters) has been discovered which are characterized by two aromatic carbamic acid ester moieties joined by an organic divalent radical. The carbamic acid ester moieties may be joined by a divalent radical through the ester group, joined by a divalent radical through a sulfur atom attached to nitrogen or joined directly to the nitrogen atoms through a divalent aromatic radical. More specifically, the compounds of the invention are characterized by the formulas:

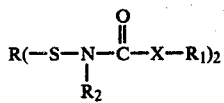

wherein X is oxygen or sulfur, $R_1$ is $C_1$–$C_{12}$ alkyl, $C_7$–$C_{10}$ aralkyl, $C_5$–$C_{12}$ cycloalkyl, or $R_2$; $R_2$ is phenyl, naphthyl and phenyl substituted by $(-R_3)_n$ wherein n is 1, 2, 3 and $R_3$ is $C_1$–$C_{12}$ alkyl, $C_1$–$C_{12}$ alkoxy, $C_1$–$C_{12}$ alkylthio, chloro, bromo, cyano or nitro, and R is $C_1$–$C_{12}$ primary or secondary alkylene or phenylene di-$C_1$–$C_6$-primary or secondary alkylene;

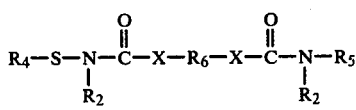

wherein X and $R_2$ are the same as before, and $R_4$ is $C_1$–$C_{12}$ primary or secondary alkyl or said alkyl radical substituted by formyl or $C_2$–$C_7$ acyl, $C_7$–$C_{10}$ aralkyl, $C_5$–$C_{12}$ cycloalkyl, or $R_2$; $R_5$ is hydrogen or $-SR_4$ and $R_6$ is phenylene, mono- or di- $C_1$–$C_6$ alkyl substituted phenylene, $C_2$–$C_6$ alkylene, phenylene-methylene, or $C_1$–$C_6$ alkylene diphenylene or $C_1$–$C_6$ alkylene di(-mono- or di-$C_1$–$C_6$ alkyl substituted phenylene), or

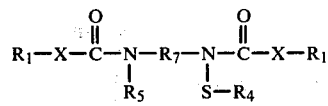

wherein X, $R_1$, $R_4$ and $R_5$ are the same as before, and $R_7$ is phenylene, mono- or di-$C_1$–$C_4$ alkyl substituted phenylene, or $C_1$–$C_6$ alkylene diphenylene. Symmetrical compounds wherein $R_5$ is $-SR_4$ are preferred.

Inhibitors of the invention may be prepared by reacting a sulfenyl chloride either with an alkali metal salt of a carbamic acid ester or with a carbamic acid ester in the presence of a hydrogen chloride acceptor. The carbamic acid ester intermediates may be prepared by reacting an isocyanate and an alcohol, preferably in the presence of an amine catalyst.

Compounds of formula A are prepared by reacting a disulfenyl chloride and an aryl carbamic acid ester or salt thereof. Compounds of formula B are prepared by reacting a monosulfenyl chloride with a di(carbamic acid ester) prepared from a diol and aryl isocyanate. Compounds of formula C are prepared by reacting a mono-sulfenyl chloride with a di(carbamic acid ester) prepared from a mono-hydric alcohol and aryl diisocyanate.

Examples of satisfactory mono-valent radicals (except $R_4$ cannot be tertiary alkyl) are:

methyl, ethyl, propyl, isopropyl, n-butyl, sec.butyl, isobutyl, t-butyl(1,1-dimethylethyl), pentyl, hexyl, heptyl, octyl, t-octyl(1,1,3,3 tetramethyl butyl), nonyl, decyl, dodecyl, cyclopentyl, cyclohexyl, 4-methylcyclohexyl, cycloheptyl, cyclooctyl, cyclodecyl, cyclododecyl, benzyl, α-methylbenzyl, α,α-dimethylbenzyl, phenethyl, phenyl, naphthyl, 4-methylphenyl, 4-chlorophenyl, 2-methyl-4-butylphenyl, 4-t-butylphenyl, 2-methylphenyl, 3-methylphenyl, 4-methoxyphenyl, 4-methylthiophenyl, and 3-isopropylphenyl. Examples of satisfactory divalent radicals are methane 1,1-diyl, ethane-1,2-diyl, 1-methylethane-1,2-diyl, propane 1,3-diyl, butane 1,4-diyl, 2-methylbutane 1,3-diyl, pentane 1,5-diyl, hexane 1,6-diyl, 1,2-phenylene, 1,3-phenylene, 1,4-phenylene, 4-methyl-1,3-phenylene, bis(1,4-phenylene)methane 1,1-diyl, bis(1,4-phenylene)-1-(methylmethane)1,1 diyl, bis(1,4-phenylene)-1,1-(dimethylmethane)-1,1-diyl, (1,3-phenylene)methane-1,1 diyl, and bis(methane 1,1 diyl)-1,4-phenylene. Examples of satisfactory acyl radicals are acetyl, propionyl, and butyryl.

Compounds in which $R_2$ is phenyl comprise a preferred subclass of inhibitors. Compounds in which $R_4$ is $C_5$–$C_8$ cycloalkyl or $C_3$–$C_8$ secondary alkyl, especially isopropyl, comprise another preferred subclass of inhibitors. Compounds in which $R_2$ is phenyl, $R_1$ is methyl, X is oxygen, and R is $C_5$–$C_8$ cycloalkyl or $C_3$–$C_8$ secondary alkyl are especially preferred.

Examples of compounds of the invention of formula (A) are:

1,2-ethanediylbis(thio)bisphenylcarbamic acid, dimethyl ester 1,3-propanediylbis(thio)bisphenylcarbamic acid, dimethyl ester 1,6-hexanediylbis(thio)bisphenylcarbamic acid, dimethyl ester 1,4-phenylenebis(methanediylthio)bisphenylcarbamic acid, dimethyl ester 1,2-ethanediylbis(thio)bisphenylcarbamic acid, diphenyl ester
1,3-propanediylbis(thio)bisphenylcarbamic acid, diphenyl ester
1,6-hexanediylbis(thio)bisphenylcarbamic acid, diphenyl ester
1,4-phenylenebis(methanediylthio)bisphenylcarbamic acid, diphenyl ester
1,2-ethanediylbis(thio)bisphenylcarbamic acid, cyclohexyl ester
1,3-propanediylbis(thio)bisphenylcarbamic acid, cyclohexyl ester
1,6-hexanediylbis(thio)bisphenylcarbamic acid, cyclohexyl ester
1,4-phenylenebis(methanediylthio)bisphenylcarbamic acid, cyclohexyl ester and the corresponding carbamothioic acid esters.

Examples of compounds of the invention of formula (B) are:

bis(Cyclohexylthio)phenylcarbamic acid, 1,3-phenylene ester
bis(Isopropylthio)phenylcarbamic acid, 1,3-phenylene ester
bis(Phenylthio)phenylcarbamic acid, 1,3-phenylene ester
bis(Cyclohexylthio)phenylcarbamic acid, 1,4-phenylene ester
bis(Isopropylthio)phenylcarbamic acid, 1,4-phenylene ester
(Phenylthio)phenylcarbamic acid, 1,4-phenylene ester
bis(Benzylthio)phenylcarbamic acid, 1,3-phenylene ester
bis(Cyclohexylthio)phenylcarbamic acid, 1,2-phenylene ester
bis(Isopropylthio)phenylcarbamic acid, 1,2-phenylene ester
bis(Phenylthio)phenylcarbamic acid, 1,2-phenylene ester
bis(Benzylthio)phenylcarbamic acid, 1,2-phenylene ester and the corresponding carbamothioic acid esters.

Examples of compounds of the invention of formula (C) are:
(4-methyl-1,3-phenylene)bis(cyclohexylthio)carbamic acid, bisphenyl ester
(4-methyl-1,3-phenylene)bis(isopropylthio)carbamic acid, bisphenyl ester
(4-methyl-1,3-phenylene)bis(phenylthio)carbamic acid, bisphenyl ester
(4-methyl-1,3-phenylene)bis(benzylthio)carbamic acid, bisphenyl ester
(4-methyl-1,3-phenylene)bis(cyclohexylthio)carbamic acid, bismethyl ester
(4-methyl-1,3-phenylene)bis(isopropylthio)carbamic acid, bismethyl ester
(4-methyl-1,3-phenylene)bis(phenylthio)carbamic acid, bismethyl ester
(4-methyl-1,3-phenylene)bis(benzylthio)carbamic acid, bismethyl ester
(4-methyl-1,3-phenylene)bis(cyclohexylthio)carbamic acid, biscyclohexyl ester
(4-methyl-1,3-phenylene)bis(isopropylthio)carbamic acid, biscyclohexyl ester
(4-methyl-1,3-phenylene)bis(phenylthio)carbamic acid, biscyclohexyl ester
(4-methyl-1,3-phenylene)bis(benzylthio)carbamic acid, biscyclohexyl ester
(1,4-phenylene)bis(cyclohexylthio)carbamic acid ester bis methyl ester
(2,2-dimethylpropane-2,2-diyl di-1,4-phenylene)bis(cyclohexylthio)carbamic acid ester, bis methyl ester and the corresponding carbamothioic acid esters.

The compounds of the invention are potent premature vulcanization inhibitors for rubber. Accordingly, one embodiment of the invention comprises vulcanizable rubber compositions comprising sulfur-vulcanizable rubber, sulfur-vulcanizing agent, organic vulcanization accelerating agent and, in an amount effective to inhibit premature vulcanization, at least one compound of the formulas (A), (B) or (C) above.

The compounds of the invention are incorporated into rubber stocks by mixing on a mill or in an internal mixer such as a Banbury mixer. However, the compounds may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur. Rubber compositions containing organic accelerating agents are particularly improved by the inhibitors of the invention. Any organic accelerating agents in an amount effective (generally about 0.1–5 parts by weight accelerator per 100 parts by weight rubber) to accelerate the sulfur vulcanization of rubber is satisfactory in the practice of this invention. Examples of suitable accelerators are described in U.S. Pat. No. 3,546,185, col. 9, lines 53–75 and in U.S. Pat. No. 3,780,001, col. 4, lines 43–72. The process of the invention is applicable to a wide variety of natural and synthetic rubbers and mixtures thereof and especially applicable to diene rubbers. Examples of satisfactory rubbers are described in U.S. Pat. No. 3,546,185, col. 10, lines 15–21 and U.S. Pat. No. 3,780,001, col. 5, lines 5–33. The vulcanizable composition may also contain conventional compounding ingredients such as reinforcing pigments, extenders, processing oils, antidegradants and the like.

Small amounts of inhbitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 part inhibitor per 100 parts rubber being normally used. Methods for determining scorch times and curing characteristics of rubber stocks used in demonstrating this invention are described in U.S. Pat. No. 3,546,185, col. 13, lines 30–53.

The compounds of formula (A) also exhibit crosslinking activity, i.e., they form cross-link between rubber molecules. Generally, 2 or more parts by weight of formula (A) compound is used per 100 parts by weight of rubber to obtain significant cross-linking.

PREFERRRED EMBODIMENTS

A suitable procedure for preparing compounds of the invention comprises adding, preferably between 0°–75° C., usually at about room temperature, a sulfenyl chloride to a slurry of a carbamic acid ester (or thiocarbamic acid ester) in an inert organic medium, such as heptane, in the presence of an acid acceptor, such as triethylamine. The amine salt by-product is removed by filtration. The filtrate is washed with water and dried with sodium sulfate. The product is recovered by evaporating the solvent and is further purified by conventional procedures.

An alternate procedure for preparing compounds of the invention comprises reacting a sulfenyl chloride and an alkali metal salt of a carbamic acid ester. The carbamic acid ester alkali metal salt intermediate may be prepared by reacting an alkali metal alcoholate and a carbamic acid ester in an inert organic medium. The alcohol by-product is stripped from the reaction mixture by distillation. The alcoholate reactant is selected so that the alcohol portion will not exchange with the ester, preferably, the alcohol portion and ester are identical. The resulting slurry of carbamic acid ester alkali metal salt may be reacted, without further purification, with the sulfenyl chloride reactant. The sulfenyl chloride is generally added dropwise at room temperature to the aforesaid slurry. Salt by-product and any unreacted carbamic acid ester alkali metal salt is removed by filtration. The product is recovered by evaporation and generally is further purified by recrystallization from an appropriate solvent, such as, hexane.

EXAMPLE 1

To a slurry of the sodium phenylcarbamic acid, methyl ester (0.2 m) and 250 ml of heptane, 1,2-ethanedisulfenyl chloride solution (0.1 m) is added dropwise at 25°–30° C. over a period of 25 minutes. The reaction mixture is stirred 35 additional minutes then filtered. The solid on the filter is washed with heptane then slurried in water. Product fraction one is recovered by filtration and air-dried. The filtrate from the reaction mixture is washed with water, dried with Na$_2$SO$_4$ and the heptane is removed by vacuum distillation. The residue is product fraction two. Product fractions one and two are combined, slurried in ethyl ether, filtered and air-dried. 1,2-Ethanediylbis(thio)bisphenylcarbamic acid, dimethyl ester, (22.6 g), m.p. 147°–148.5° C., is recovered. Chemical analysis gives 16.50% sulfur compared with 16.34% sulfur calculated for $C_{18}H_{20}N_2O_4S_2$.

EXAMPLE 2

Cyclohexanesulfenyl chloride (0.2 m) as a solution in heptane is added at 24°–26° C. over 45 minutes to a stirred slurry comprising 34.6 g (0.1 m) bisphenylcarbamothioic acid, S,S'-1,3-propanediyl ester, 20.4 g triethylamine and 200 ml of heptane. After stirring 45 additional minutes, water, 200 ml, is added. The reaction mixture is filtered to remove some unreacted ester. The heptane layer of the filtrate is washed twice with water, dried over Na$_2$SO$_4$, and the heptane is removed by vacuum distillation. The partially solidified residue (45 g.) is identified by Infrared Analysis as the product indicated below. The crude product is slurred in ethylether, filtered and air-dried. Bis(cyclohexylthio)-phenylcarbamothioic acid, S,S'-1,3-propanediyl ester, m.p. 98°–98.5° C., is recovered. Analysis gives 22.38% sulfur compared with 22.31% sulfur calculated for $C_{29}H_{38}N_2O_2S_4$.

EXAMPLE 3

Benzenesulfenyl chloride (0.2 m) in toluene is added at about 19° C. over about one hour to a stirred slurry comprising bisphenylcarbamic acid, 1,3-phenylene ester, 34.8 g. (0.1 m), triethylamine, 22 g., and 200 ml of toluene. The mixture is filtered to remove salt by-product. The filtrate is washed with water, dried with NA$_2$SO$_4$, and the toluene removed by vacuum distillation to give 58 g. of solid crude product. The crude product is washed with hexane, filtered and air-dried. Bis(phenylthio)phenylcarbamic acid, 1,3-phenylene ester (42.1 g.), m.p. 121.5° C. recrystallized from toluene, is recovered. Analysis gives 11.20% sulfur compared with 11.33% sulfur calculated for $C_{32}H_{24}N_2O_4S_2$.

EXAMPLE 4

A toluene solution of cyclohexanesulfenyl chloride (0.2 m) is added at 15° C. to a slurry comprising 4-methyl-1,3-phenylene-biscarbamic acid, diphenyl ester, 36.5 g (0.1 m), triethylamine, 22 g., and 200 ml of toluene. After stirring the reaction mixture about 1.5 hours, the salt by-product is removed by filtration. The filtrate is vacuum distilled to remove toluene. The residue is dissolved in ether, washed with water, dried over Na$_2$SO$_4$ and the ether removed by evaporation to give a resinous mass. The mass is digested in ether from which a white solid precipitates. The precipitate is recovered by filtration. (4-Methyl-1,3-phenylene)bis-(cyclohexylthio)carbamic acid, diphenyl ester, m.p. 118° C., is recovered. Analysis gives 11.22% sulfur compared with 10.83% sulfur calculated for $C_{33}H_{38}N_2O_4S_2$.

Other compounds prepared in a similar manner are shown in Table 1. The intermediate for example 15 is prepared by reacting phenylisocyanate and 4,4'-butylidenebis(6-tert-butyl-m-cresol).

Table 1

| Example No. | Name | Melting Point, °C. | Sulfur Analysis, % Calc. | Found |
|---|---|---|---|---|
| 5 | (4-Methyl-1,3-phenylene)bis-(cyclohexylthio)carbamothioic acid,S,S'-bis(1,1-dimethylethyl) ester | 137–138 | 21.63 | 21.40 |
| 6 | bis(Cyclohexylthio)phenyl-carbamothioic acid, S,S'-1,2-ethanediyl ester | 106.5–107 | 22.87 | 23.10 |
| 7 | Methylenebis(1,4-phenylene)-bis(cyclohexylthio)carbamothioic acid, S,S'-bis(1,1-dimethylethyl)ester | 137–138 | 19.46 | 19.35 |
| 8 | 1,2-Ethanediylbis(thio)bis-phenylcarbamic acid, diphenyl ester | 161 | 12.41 | 12.43 |
| 9 | (4-Methyl-1,3-phenylene)bis-(cyclohexylthio)carbamic acid, dimethyl ester[1] | resinous solid | — | — |

Table 1-continued

| Example No. | Name | Melting Point, °C. | Sulfur Analysis, % Calc. | Sulfur Analysis, % Found |
|---|---|---|---|---|
| 10 | Methylenebis(1,4-phenylene)-bis(cyclohexylthio)carbamic acid,dimethyl ester[1] | resinous solid | — | — |
| 11 | bis(Cyclohexylthio)phenylcarbamic acid, 1,3-phenylene ester | resinous solid | 11.85 | 11.43 |
| 12 | bis(Isopropylthio)phenylcarbamic acid, 1,3-phenylene ester | 124–125 | 12.91 | 13.48 |
| 13 | (4-Methyl-1,3-phenylene)bis-(phenylthio)carbamic acid, diphenyl ester | 123.5–124 | 11.08 | 10.55 |
| 14 | bis(Cyclohexylthio)phenylcarbamic acid, 1,2-phenylene ester[1] | resinous solid | 11.12 | 11.03 |
| 15 | bis(Cyclohexylthio)phenylcarbamic acid, butane-1,1-diyl-di[2-(1,1-dimethylethyl)-5-methyl-1,4-phenylene]ester | resinous solid | 7.55 | 8.70 |
| 16 | bis(Cyclohexylthio)phenyl-carbamic acid, 1,4-phenylene ester | 162–163 | 11.12 | 9.75 |
| 17 | (Phenylthio)phenylcarbamic acid, 1,4-phenylene ester | 169–171 | 7.02 | 6.75 |
| 18 | (Phenylthio)phenylcarbamic acid, 1,2-phenylene ester[2] | 141–141.5 | 7.02 | 6.66 |
| 19 | bis(Phenylthio)phenylcarbamic acid, 1,4-phenylene ester[3] | 182°–197° C. | 11.36 | 10.34 |

[1] Liquid chromograph analysis indicates minor amount of mono-cyclohexylthio derivative present.
[2] Liquid chromograph analysis indicates minor amount of mono-phenylthio derivative present.
[3] Liquid chromograph analysis indicates about 17% of mono-phenylthio derivative present.

The process of the invention is demonstrated by using the following natural rubber and synthetic rubber stocks.

| | Stocks NR | Stocks SBR/PB |
|---|---|---|
| Smoked Sheets | 100 | — |
| Oil-extended styrene-butadiene rubber 1712 | — | 89 |
| Cis-4-polybutadiene rubber | — | 35 |
| Carbon Black | 45 | 67 |
| Zinc Oxide | 3 | 3 |
| Stearic Acid | 2 | 1 |
| Processing Oil | 5 | 15 |
| Wax | — | 2 |
| N-(1,3-dimethylbutyl)-N'-(phenyl)-p-phenylenediamine | 2 | 2 |
| Sulfur | 2.5 | 2.0 |
| N-(tert-butyl)-2-benzothiazole-sulfenamide | 0.5 | 1.2 |
| | 160 | 217.2 |

Portions of the masterbatches containing no inhibitors are controls. A quantity of inhibitor is incorporated into other portions of the masterbatches. The properties of the vulcanizable compositions are measured by conventional methods as described above. The results are shown in Tables 2–6.

Table 2

| Stocks | 1 | 2 | 3 | 4 | 5 | 6 | 7 |
|---|---|---|---|---|---|---|---|
| NR stocks | 160 | 160 | 160 | 160 | 160 | — | — |
| SBR/PB | — | — | — | — | — | 217.2 | 217.2 |
| 1,2-ethanediylbis(thio)bisphenyl-carbamic acid, dimethylester | — | 0.3 | — | — | — | — | — |
| 1,2-ethanediylbis(thio)bisphenyl-carbamic acid, diphenylester | — | — | 0.3 | — | — | — | — |
| bis(Cyclohexylthio)phenylcarbamo-thioic acid, S,S'-1,2-ethane-diyl ester | — | — | — | 0.3 | — | — | — |
| bis(Cyclohexylthio)phenylcarbamo-thioic acid, S,S'-1,3-propane-diyl ester | — | — | — | — | 0.3 | — | — |
| 1,2-ethanediylbis(thio)bisphenyl-carbamic acid, dimethyl ester | — | — | — | — | — | — | 0.5 |
| Mooney Scorch @ 121° C. | | | | | | | |
| $t_5$, minutes | 27.9 | 53.8 | 44.1 | 38.4 | 38.4 | — | — |
| % increase in scorch delay | — | 93 | 58 | 38 | 38 | — | — |
| Mooney Scorch @ 135° C. | | | | | | | |
| $t_5$, minutes | — | — | — | — | — | 23.0 | 35.8 |
| % increase in scorch safety | — | — | — | — | — | — | 56 |
| Stress-Strain @ 153° C. | | | | | | | |
| $M_{300}$, MPa | 11.5 | 11.3 | 11.6 | 11.4 | 11.7 | 8.6 | 9.0 |
| UTS, MPa | 28.9 | 29.9 | 28.8 | 27.6 | 28.8 | 20.2 | 20.2 |
| Elong., % | 570 | 580 | 560 | 540 | 570 | 570 | 570 |

TABLE 3

| Stocks | 1 | 2 | 3 | 4 |
|---|---|---|---|---|
| NR stocks | 160 | 160 | 160 | 160 |
| bis(Phenylthio)phenyl-carbamic acid, 1,3-phenylene ester | — | 0.3 | — | — |
| bis(Cyclohexylthio)phenyl-carbamic acid, 1,3-phenylene ester | — | — | 0.3 | — |
| bis(Isopropylthio)phenyl-carbamic acid, 1,3-phenylene ester | — | — | — | 0.3 |
| Mooney Scorch @ 121° C. | | | | |
| $t_5$, minutes | 33.3 | 52.5 | 56.5 | 71.1 |
| % increase in scorch delay | — | 58 | 70 | 114 |
| Stress-Strain @ 153° C. | | | | |
| $M_{300}$, MPa | 11.5 | 10.6 | 10.4 | 11.0 |
| UTS, MPa | 30.4 | 28.1 | 28.8 | 28.0 |
| Elong., % | 600 | 600 | 610 | 580 |

Table 4

| Stocks | 1 | 2 | 3 | 4 | 5 | 6 | 7 | 8 | 9 |
|---|---|---|---|---|---|---|---|---|---|
| NR stocks | 160 → | | | | | | | | |
| (4-methyl-1,3-phenylene)bis-(cyclohexylthio)carbamic acid, dimethyl ester | — | 0.3 | — | — | — | — | — | — | — |
| Methylenebis(1,4-phenylene)bis-(cyclohexylthio)carbamic acid, dimethyl ester | — | — | 0.3 | — | — | — | — | — | — |
| (4-methyl-1,3-phenylene)bis-(cyclohexylthio)carbamic acid, diphenyl ester | — | — | — | — | 0.3 | — | — | — | — |
| (4-methyl-1,3-phenylene)bis-(phenylthio)carbamic acid, diphenyl ester | — | — | — | — | — | 0.3 | — | — | — |
| (4-methyl-1,3-phenylene)bis-(cyclohexylthio)carbamothioic acid, S,S'-bis(1,1-dimethylethyl)ester | — | — | — | — | — | — | — | 0.3 | — |
| Methylenebis(1,4-phenylene)bis-(cyclohexylthio)carbamothioic acid, S,S'-bis(1,1-dimethylethyl)ester | — | — | — | — | — | — | — | — | 0.3 |
| Mooney Scorch @ 121° C. | | | | | | | | | |
| $t_5$, minutes | 36.1 | 60.9 | 47.4 | 31.5 | 57.2 | 50.7 | 27.9 | 40.2 | 40.9 |
| % increase in scorch delay | — | 69 | 31 | — | 82 | 61 | — | 44 | 47 |
| Stress-Strain @ 153° C. | | | | | | | | | |
| M300, MPa | 10.8 | 11.5 | 11.7 | 12.1 | 9.6 | 9.8 | 11.5 | 11.7 | 11.9 |
| UTS, MPa | 29.4 | 30 | 29.1 | 28.7 | 28.6 | 28.5 | 28.9 | 28.4 | 28.7 |
| Elong., % | 600 | 610 | 590 | 560 | 620 | 600 | 570 | 540 | 560 |

Table 5

| Stocks | 1 | 2 | 3 | 4 | 5 | 6 |
|---|---|---|---|---|---|---|
| NR stocks | 160 → | | | | | |
| bis(Cyclohexylthio)phenyl carbamic acid, 1,2-phenylene ester | — | 0.3 | — | — | — | — |
| bis(Cyclohexylthio)phenyl carbamic acid, 1,4-phenylene ester | — | — | 0.3 | — | — | — |
| (Phenylthio)phenyl carbamic acid, 1,4-phenylene ester | — | — | — | 0.3 | — | — |
| (Phenylthio)phenyl carbamic acid, 1,2-phenylene ester | — | — | — | — | 0.3 | — |
| bis(Phenylthio)phenylcarbamic acid, 1,4-phenylene ester | — | — | — | — | — | 0.3 |
| Mooney Scorch @ 121° C. | | | | | | |
| $t_5$, minutes | 31.5 | 51.3 | 53.5 | 41.5 | 38.5 | 47.5 |
| % increase in scorch delay | — | 63 | 70 | 32 | 22 | 51 |
| Stress-Strain @ 153° C. | | | | | | |
| $M_{300}$, MPa | 12.1 | 9.9 | 9.3 | 8.8 | 9.4 | 9.2 |
| UTS, MPa | 28.7 | 29.1 | 26.1 | 27.0 | 28.2 | 27.7 |
| Elong., % | 560 | 620 | 580 | 620 | 630 | 640 |

Table 6

| Stocks | 1 | 2 |
|---|---|---|
| NR stock | 160 | 160 |
| bis(Cyclohexylthio)phenylcarbamic acid, butane 1,1-diyl-di[2-(1,1-dimethylethyl)-5-methyl-1,4-phenylene)ester | — | 0.3 |
| Mooney Scorch @ 121° C. | | |
| $t_5$, minutes | 25.0 | 36.2 |
| % increase in scorch delay | — | 45 |
| Stress-Strain @ 153° C. | | |
| $M_{300}$, MPa | 12.5 | 11.1 |
| UTS, MPa | 29.3 | 27.8 |
| Elong., % | 570 | 570 |

Referring to Table 2, stock 1 is a control showing a natural rubber stock without inhibitor and stock 6 is a control showing a synthetic rubber stock without inhibitor. Stocks 2, 3 and 7 show that alkylenebis(thio)bis-phenylcarbamic acid esters are potent premature vulcanization inhibitors. Comparison of the data of stocks 2 and 3 indicates that the dimethyl ester is more potent than the diphenyl ester. Stocks 4 and 5 show the inhibitor activity of bis(cyclohexylthio)phenylcarbamothioic acid, S,S'-alkanediyl esters.

The inhibitor activity of N(thio)phenylcarbamic acid, 1,3-phenylene esters is illustrated in Table 3. The data show that the isopropylthio compound is about twice as effective as the corresponding phenylthio compound.

Compounds of the invention derived from biscarbamic acid esters and biscarbamothioic acid esters are demonstrated as effective inhibitors in Table 4.

The inhibitor activity of bisphenylcarbamic acid, phenylene esters is illustrated in Table 5. The data show that two thio substituents enhances the inhibitor activity. Compare stocks 4 and 6.

The inhibitor activity of the compound of Example 15 is illustrated in Table 6. The data show that 0.3 parts of the inhibitor increase the scorch delay by 45 percent.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A vulcanizable rubber composition inhibited from premature vulcanization comprising sulfur-vulcanizable rubber, sulfur vulcanizing agent, organic vulcanization accelerating agent, and, in an amount effective to inhibit premature vulcanization, a compound of the formula

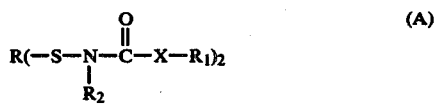

wherein X is oxygen or sulfur, $R_1$ is $C_1-C_{12}$ alkyl, $C_7-C_{10}$ aralkyl, $C_5-C_{12}$ cycloalkyl, or $R_2$; $R_2$ is phenyl, naphthyl and phenyl substituted by $(-R_3)_n$ wherein n is 1, 2, 3 and $R_3$ is $C_1-C_{12}$ alkyl, $C_1-C_{12}$ alkoxy, $C_1-C_{12}$ alkylthio, chloro, bromo, cyano or nitro, and R is $C_1-C_{12}$ primary or secondary alkylene or phenylene di-$C_1-C_6$-primary or secondary alkylene;

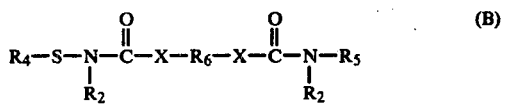

wherein X and $R_2$ are the same as before, and $R_4$ is $C_1-C_{12}$ primary or secondary alkyl or said alkyl radical substituted by formyl or $C_2-C_7$ acyl, $C_7-C_{10}$ aralkyl, $C_5-C_{12}$ cycloalkyl, or $R_2$; $R_5$ is hydrogen or —$SR_4$ and $R_6$ is phenylene, mono- or di- $C_1-C_6$ alkyl substituted phenylene, $C_2-C_6$ alkylene, phenylene-methylene, or $C_1-C_6$ alkylene diphenylene or $C_1-C_6$ alkylene di(-mono- or di-$C_1-C_6$ alkyl substituted phenylene), or

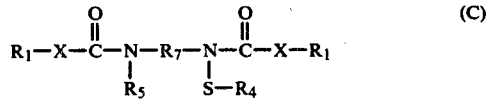

wherein X, $R_1$, $R_4$ and $R_5$ are the same as before, and $R_7$ is phenylene, mono- or di-$C_1-C_4$ alkyl substituted phenylene, or $C_1-C_6$ alkylene diphenylene.

2. The composition of claim 1 in which the vulcanizing agent is elemental sulfur and the rubber is a diene rubber.

3. The composition of claim 2 comprising a compound of formula (A).

4. The composition of claim 3 in which X is oxygen.

5. The composition of claim 4 in which R is $C_2-C_6$ alkylene.

6. The composition of claim 5 in which $R_1$ is $C_1-C_6$ alkyl, cyclohexyl or phenyl.

7. The composition of claim 6 in which $R_1$ and $R_2$ are phenyl.

8. The composition of claim 6 in which $R_1$ is methyl and $R_2$ is phenyl.

9. The composition of claim 7 in which R is ethane-1,2-diyl.

10. The composition of claim 8 in which R is ethane-1,2-diyl.

11. The composition of claim 3 in which X is sulfur, and $R_1$ is $C_1-C_6$ alkyl, cyclohexyl or phenyl.

12. The composition of claim 11 in which $R_1$ is methyl and $R_2$ is phenyl.

13. The composition of claim 11 in which $R_1$ and $R_2$ are phenyl.

14. The composition of claim 2 comprising a compound of formula (B).

15. The composition of claim 14 in which X is oxygen, $R_4$ is $C_1-C_6$ alkyl, cyclohexyl or phenyl, $R_5$ is —$SR_4$, and $R_6$ is phenylene.

16. The composition of claim 15 in which $R_2$ is phenyl.

17. The composition of claim 16 in which $R_4$ is cyclohexyl.

18. The composition of claim 16 in which $R_4$ is isopropyl.

19. The composition of claim 2 comprising a compound of formula (C).

20. The composition of claim 19 in which X is oxygen, $R_1$ and $R_4$ independently are $C_1-C_6$ alkyl, cyclohexyl or phenyl, $R_5$ is —$SR_4$, and $R_7$ is phenylene or mono- alkyl substituted phenylene.

21. The composition of claim 20 in which $R_2$ is 1,3-phenylene or mono- alkyl substituted 1,3-phenylene, and $R_1$ is methyl.

22. The composition of claim 21 in which $R_4$ is cyclohexyl.

23. The composition of claim 21 in which $R_4$ is isopropyl.

24. A method of inhibiting premature vulcanization of sulfur vulcanizable rubber containing a sulfur vulcanizing agent and organic vulcanization accelerating agent which comprises incorporating therein, in an amount effective to inhibit premature vulcanization, a compound of the formulas

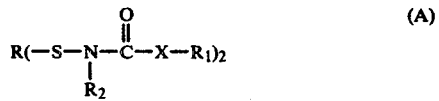

wherein X is oxygen or sulfur, $R_1$ is $C_1-C_{12}$ alkyl, $C_7-C_{10}$ aralkyl, $C_5-C_{12}$ cycloalkyl, or $R_2$; $R_2$ is phenyl, naphthyl and phenyl substituted by $(-R_3)_n$ wherein n is 1, 2, 3 and $R_3$ is $C_1-C_{12}$ alkyl, $C_1-C_{12}$ alkoxy, $C_1-C_{12}$ alkylthio, chloro, bromo, cyano or nitro, and R is $C_1$-$C_{12}$ primary or secondary alkylene or phenylene di-$C_1$-$C_6$-primary or secondary alkylene;

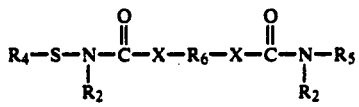

wherein X and $R_2$ are the same as before, and $R_4$ is $C_1$-$C_{12}$ primary or secondary alkyl or said alkyl radical substituted by formyl or $C_2$-$C_7$ acyl, $C_7$-$C_{10}$ aralkyl, $C_5$-$C_{12}$ cycloalkyl, or $R_2$; $R_5$ is hydrogen or —$SR_4$ and $R_6$ is phenylene, mono- or di-$C_1$-$C_6$ alkyl substituted phenylene, $C_2$-$C_6$ alkylene, phenylene-methylene, or $C_1$-$C_6$ alkylene diphenylene or $C_1$-$C_6$ alkylene di(-mono- or di-$C_1$-$C_6$ alkyl substituted phenylene), or

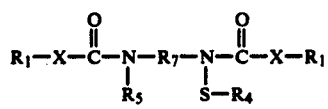

wherein X, $R_1$, $R_4$ and $R_5$ are the same as before, and $R_7$ is phenylene, mono- or di-$C_1$-$C_4$ alkyl substituted phenylene, or $C_1$-$C_6$ alkylene diphenylene.

25. The method of claim 24 in which the vulcanizing agent is elemental sulfur and the rubber is a diene rubber.

26. A compound of the formulas

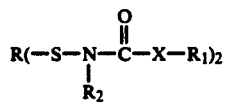

wherein X is oxygen or sulfur, $R_1$ is $C_1$-$C_{12}$ alkyl, $C_7$-$C_{10}$ aralkyl, $C_5$-$C_{12}$ cycloalkyl, or $R_2$; $R_2$ is phenyl, naphthyl and phenyl substituted by $(-R_3)_n$ wherein n is 1, 2, 3 and $R_3$ is $C_1$-$C_{12}$ alkyl, $C_1$-$C_{12}$ alkoxy, $C_1$-$C_{12}$ alkylthio, chloro, bromo, cyano or nitro, and R is $C_1$-$C_{12}$ primary or secondary alkylene or phenylene di-$C_1$-$C_6$-primary or secondary alkylene;

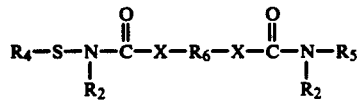

wherein X and $R_2$ are the same as before, and $R_4$ is $C_1$-$C_{12}$ primary or secondary alkyl or said alkyl radical substituted by formyl or $C_2$-$C_7$ acyl, $C_7$-$C_{10}$ aralkyl, $C_5$-$C_{12}$ cycloalkyl, or $R_2$; $R_5$ is hydrogen or —$SR_4$ and $R_6$ is phenylene, mono- or di-$C_1$-$C_6$ alkyl substituted phenylene, $C_2$-$C_6$ alkylene, phenylenemethylene, or $C_1$-$C_6$ alkylene diphenylene or $C_1$-$C_6$ alkylene di(-mono- or di-$C_1$-$C_6$ alkyl substituted phenylene), or

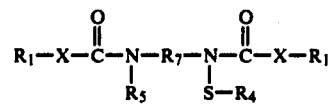

wherein X, $R_1$, $R_4$ and $R_5$ are the same as before, and $R_7$ is phenylene, mono- or di-$C_1$-$C_4$ alkyl substituted phenylene, or $C_1$-$C_6$ alkylene diphenylene.

27. The compound of claim 26, formula (A).
28. The compound of claim 27 in which X is oxygen.
29. The compound of claim 28 in which R is $C_2$-$C_6$ alkylene.
30. The compound of claim 29 in which $R_1$ is $C_1$-$C_6$ alkyl, cyclohexyl or phenyl.
31. The compound of claim 30 in which $R_1$ and $R_2$ are phenyl.
32. The compound of claim 29 in which $R_1$ is methyl and $R_2$ is phenyl.
33. The compound of claim 31 in which R is ethane-1,2-diyl.
34. The compound of claim 32 in which R is ethane-1,2-diyl.
35. The compound of claim 27 in which X is sulfur, and $R_1$ is $C_1$-$C_6$ alkyl, cyclohexyl or phenyl.
36. The compound of claim 35 in which $R_1$ is methyl and $R_2$ is phenyl.
37. The compound of claim 35 in which $R_1$ and $R_2$ are phenyl.
38. The compound of claim 26 comprising a compound of formula (B).
39. The compound of claim 38 in which X is oxygen, $R_4$ is $C_1$-$C_6$ alkyl, cyclohexyl or phenyl, $R_5$ is —$SR_4$, and $R_6$ is phenylene.
40. The compound of claim 39 in which $R_2$ is phenyl.
41. The compound of claim 40 in which $R_4$ is isopropyl.
42. The compound of claim 26 comprising a compound of formula (C).
43. The compound of claim 42 in which X is oxygen, $R_1$ and $R_4$ independently are $C_1$-$C_6$ alkyl, cyclohexyl or phenyl, $R_5$ is —$SR_4$, and $R_7$ is phenylene or mono- alkyl substituted phenylene.
44. The compound of claim 43 in which $R_2$ is 1,3-phenylene or mono- alkyl substituted 1,3-phenylene, and $R_1$ is methyl.
45. The compound of claim 44 in which $R_4$ is cyclohexyl.
46. The compound of claim 44 in which $R_4$ is isopropyl.

* * * * *